(12) United States Patent
Klein et al.

(10) Patent No.: US 7,374,942 B2
(45) Date of Patent: May 20, 2008

(54) PROCESS AND APPARATUS FOR THE COMBINATORIAL PRODUCTION AND TESTING OF CATALYST MATERIAL LIBRARIES BY USING AT LEAST TWO ANALYTICAL METHODS

(75) Inventors: Jens Klein, Heidelberg (DE); Wolfram Stichert, Heidelberg (DE); Wolfgang Strehlau, Dossenheim (DE); Armin Brenner, Spiesheim (DE); Stephan Andreas Schunk, Heidelberg (DE); Dirk Demuth, Nussloch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 79 days.

(21) Appl. No.: 09/809,423

(22) Filed: Mar. 16, 2001

(65) Prior Publication Data
US 2001/0053530 A1   Dec. 20, 2001

(30) Foreign Application Priority Data
Mar. 16, 2000  (DE) ............................ 100 12 847

(51) Int. Cl.
*G01N 31/10* (2006.01)
*G01N 30/88* (2006.01)
*B01D 59/44* (2006.01)

(52) U.S. Cl. .................... 436/37; 250/282; 422/78; 422/80; 422/89; 422/129; 422/130; 436/139; 436/140; 436/141; 436/142; 436/151; 436/152; 436/155; 436/159; 436/161; 436/171; 436/172; 436/173; 436/181

(58) Field of Classification Search .............. 436/37, 436/139–142, 147, 149, 155, 157, 159, 161, 436/171–173, 181; 250/281–282; 422/68.1, 422/78, 80, 83, 86, 88–94, 129, 130
See application file for complete search history.

(56) References Cited

U.S. PATENT DOCUMENTS
5,356,756 A * 10/1994 Cavicchi et al. ............ 430/315
(Continued)

FOREIGN PATENT DOCUMENTS
DE    198 30 607 A1    1/2000
(Continued)

OTHER PUBLICATIONS
Albaugh, E. W. et al, Analytical Chemistry 1976, 48, 1579-1582.*
(Continued)

*Primary Examiner*—Arlen Soderquist
(74) *Attorney, Agent, or Firm*—Oblon, Spivak, McClelland, Maier & Neustadt, P.C.

(57) ABSTRACT

A process and apparatus for testing material libraries, in particular catalysts, by means of coupled use of at least two analytical methods, preferably IR thermography and mass spectrometry. Owing to the selected arrangement, the disadvantages of the two previously known individual methods are compensated for: the subsequent selectivity determination for selected sections by means of mass spectrometry invalidates the argument against IR thermography, of only being able to determine activities; the rapid integrated determination of potentially "good" materials via IR thermography prevents an excessive loss of time by needing to test all materials of a library successively with the mass spectrometer. The reactor design permits, firstly, the integral recording of the entire reactor through a window which is transparent for the corresponding method and, secondly, permits the simultaneous, automated application of a second analytical method (for example mass spectrometry) to selected materials of a material library, which have been rated as active by the optical method. In the case described, the optical method provides information on the material activity for a set problem, and the second analytical method determines the selectivity of the materials.

26 Claims, 1 Drawing Sheet

U.S. PATENT DOCUMENTS

| | | | |
|---|---|---|---|
| 5,449,754 A | 9/1995 | Nishioka | 530/334 |
| 5,959,297 A | 9/1999 | Weinberg et al. | 250/288 |
| 5,985,356 A | 11/1999 | Schultz et al. | 427/8 |
| 6,004,617 A | 12/1999 | Schultz et al. | 427/8 |
| 6,063,633 A * | 5/2000 | Willson, III | 436/37 |
| 6,306,349 B1 * | 10/2001 | Moon et al. | 422/69 |
| 6,426,226 B1 * | 7/2002 | Senkan | 436/37 |
| 6,508,984 B1 * | 1/2003 | Turner et al. | 422/65 |
| 6,537,500 B1 | 3/2003 | Brenner et al. | |
| 6,541,271 B1 * | 4/2003 | McFarland et al. | 436/171 |
| 6,576,470 B1 * | 6/2003 | Windhab et al. | 436/64 |
| 6,627,445 B1 * | 9/2003 | Akporiaye et al. | 436/37 |

FOREIGN PATENT DOCUMENTS

| | | |
|---|---|---|
| DE | 19839891 | 1/2000 |
| EP | 623820 | 11/1994 |
| WO | 96/11878 | 4/1996 |
| WO | 97/32208 | 9/1997 |
| WO | 98/15813 | 4/1998 |
| WO | 98/15969 | 4/1998 |
| WO | 99/19724 | 4/1999 |
| WO | 99/41005 | 9/1999 |

OTHER PUBLICATIONS

Fawcett, t. Chemtech 1987, 17, 564-569.*
Guyer, A., Jr. Chimia 1967, 21, 134-135.*
Hogan, R. J. et al, Preprints—American Chemical Society, Division of Petroleum Chemistry 1971, 16, D35-D42.*
Borodzinski, A. et al, Reaction Kinetics and Catalysis Letters 1977, 7, 163-169.*
Latzel, J. Reaction Kinetics and Catalysis Letters 1977, 7, 393-396.*
Stockinger, J. H. et al, Journal of Chromatographic Science 1978, 16, 418-426.*
Vannice, M. A. et al, Journal of Physics E: Scientific Instruments 1979, 12, 849-852.*
Miura, H. et al, Journal of Physics E: Scientific Instruments 1982, 15, 373-377.*
Ganschow, O. et al, Journal of Vacuum Science & Technology, A 1983, 1, 1491-1506.*
Karge, H. G. et al, Int. Congr. Catal., [Proc.], 8th 1985, Meeting Date 1984, vol. 3, III 453-III 463 Publisher: Verlag Chemie, Weinheim, Fed. Rep. Ger.*
Borgmann, D. et al, Chemie Ingenieur Technik 1986, 58, 400-402.*
Watanabe, M. et al, Applied Surface Science 1987, 28, 147-166.*
Newman, R. A. et al, Materials Research Society Symposium Proceedings 1988, 111(Microstruct. Prop. Catal.), 405-411.*
Topsoe, N. Y. et al, Catalysis Today 1991, 9, 77-82.*
Clausen, B. S. et al, Journal of Catalysis 1991, 132, 524-535.*
Puxley, D. C. et al, Journal of Applied Crystallography 1994, 27, 585-594.*
Williams, C. T. et al, Journal of Catalysis 1996, 163, 63-76.*
Deng, Y. et al, Faraday Discussions 1996, 105, 33-46.*
Ozkan, U. S. et al, Journal of Catalysis 1997, 171, 67-76.*
LeBlond, C. et al, Topics in Catalysis 1998, 5, 149-158.*
Hunger, M et al, Catalysis Letters 1999, 57, 199-204.*
Rogers, Donald Evan Sciencaj Komunikajoj 1986, 11, 44-52.*
Kaul, D. J. et al, Chemical Engineering Science 1987, 42, 1399-1411.*
Drechsler, G. et al, Journal of Molecular Structure 1995, 348, 337-340.*
Arnold, M. R. et al, Industrial and Engineering Chemistry 1952, 44, 999-1003.*
Choudhary, V. R. et al, Journal of Catalysis 1971, 23, 54-60.*
Anderson, D. N. NASA Tech. Memo. 1976, NASA-TM-X-73410, 21 pages.*
Jain, S. et al, Adv. Catal., [Proc.—Natl. Symp. Catal.], 7th 1985, 383-387, Editor: Prasada Rao, T. S. R., Publisher: Wiley, New York.*
Forni, L. et al, Applied Catalysis 1987, 29, 161-174.*
Gachet, C. et al, Catalysis Today 1988, 4, 7-22.*
Alyea, E. C. et al, Studies in Surface Science and Catalysis 1992, 73, 309-314.*
Slagtern, A, et al, Applied Catalysis, A: General 1992, 91, 13-25.*
Topsoe, N. Y. et al, Journal of Catalysis 1995, 151, 226-240.*
TamizhMani, G. et al, Journal of Electroanalytical Chemistry 1998, 444, 121-125.*
Dossi, C. et al, Thermochimica Acta 1998, 317, 157-164.*
Gilbert, W. R. Preprints—American Chemical Society, Division of Petroleum Chemistry 1999, 44, 534-536.*
Stone, R. L. et al, Analytical Chemistry 1957, 29, 1273-1277.*
Evans, D. A. et al, Tetrahedron Letters 1996, 37, 7481-7484.*
Shen, S.-T. et al, Industrial & Engineering Chemistry Research 1998, 37, 2654-2661.*
Senkan, S. M., Nature 1998, 394, 350-353.*
Riedel, T. et al, Applied Catalysis A: General 1999, 186, 201-213.*
Cong, P. et al, Proceedings of the National Academy of Sciences of the United States of America 1999, 96, 11077-11080.*
Musa, Z. et al, Latvijas PSR Zinatnu Akademijas Vestis, Kimijas Serija 1970, 743-745.*
Burch, R. et al, Applied Catalysis 1988, 43, 105-116.*
Nakamura, R. et al, Catalysis Today 1991, 10, 119-129.*
Sin, W. D. et al, Oxidation Communications 1992, 15, 115-126.*
Moates, F. C. et al, Industrial & Engineering Chemistry Research 1996, 35, 4801-4803.*
Brenner et al., "Method for Detecting Product Based On One From Among Plural Catalyst Materials," Patent Abstracts of Japan, 2000-193653, Jul. 14, 2000, (Abstract Only).
Moates, F.C. et al., "Infrared Thermographic Screening of Combinatorial Libraries of Heterogeneous Catalysts", Ind. Eng. Chem. Res., vol. 35, No. 12, © 1996 American Chemical Society, pp. 4801-4803, (1996).
SERVICE, Robert F., "The Fast Way to a Better Fuel Cell", Science, vol. 280, pp. 1690-1691, (Jun. 12, 1998).
Abstract of A 15 (3 pages), abstract of Holzwarth, Arnold, et al., "IR-thermographische Erkennung Katalytischer Aktivitaet in Kombinatortschen Bibliotheken Heterogener Katalysatoren", Angew. Chem. 110 (19), pp. 2788-2792 (1998).
Cong, Peijun, et al., "High-Throughput Synthesis and Screening of Combinatorial Heterogeneous Catalyst Libraries", Angew. Chem. Int. Ed. 38, No. 4, pp. 483-488 (1999).
Orschel, Matthias, et al., "Detection of Reaction Selectivity on Catalyst Libraries by Spatially Resolved Mass Spectrometry", Angew. Chem. Int. Ed. 38, No. 18, pp. 2791-2794 (1999).
Holzwarth, Arnold et al, IR-thermographische Erkennung katalytischer Aktivitaet in kombinatorischen Bibliotheken heterogener Katalysatoren, Angew. Chem. 110, No. 19, ©WILEY-VCH Verlag GmbH, pp.
Cong, Peijun et al., "Kombinatorische Parallelsynthese und Hochgeschwindigkeitsrasterung von Heterogenkatalysator-Bibliotheken", Angew. Chem. 111, No. 4, ©WILEY-VCH Verlag GmbH, pp. 508-512, (1999).
Orschel, Matthias et al., "Erkennung der Selektivitaet von Oxidationsreaktionen auf Katalysatorbibliotheken durch ostsaufgeloeste Massenspektrometrie", Angew. Chem. 111, No. 18, ©WILEY-VCH Verlag GmbH, pp. 29612965, (1999).

* cited by examiner

PROCESS AND APPARATUS FOR THE COMBINATORIAL PRODUCTION AND TESTING OF CATALYST MATERIAL LIBRARIES BY USING AT LEAST TWO ANALYTICAL METHODS

CROSS REFERENCE TO RELATED APPLICATION

The present application claims benefit of priority of German Patent Application No. 100 12 847.5, filed on Mar. 16, 2000, incorporated herein by reference in its entirety.

BACKGROUND OF THE INVENTION

The present invention relates to a process for the combinatorial production of material libraries and testing of the same using at least two analytical methods and to an apparatus for carrying out this process.

Combinatorial methods have been for some time the centre of interest of research and development in the field of material research. Using these combinatorial methods, as great a number as possible of different or identical chemical compounds are always prepared and thus a material library is produced which are then investigated for useful properties using a suitable method. In addition to magnetic, electronic, electromagnetic, optical, electrooptical, electromechanical properties etc., interest also centres on catalytical properties of such materials prepared by combinatorial or highly parallel methods. In this context we refer to WO 99/41005 and the prior art cited therein. This publication relates to arrays of heterogeneous catalysts and/or their precursors, built up from a body which has preferably parallel continuous channels and in which at least n channels contain n different heterogeneous catalysts and/or their precursors, where n has the value 2, preferably 10, particularly preferably 100, in particular 1000, especially 10,000. Furthermore, the publication relates to a process for preparing such arrays and to a process for determining the activity, selectivity and/or long-term stability of catalysts in such an array.

Relatively large material libraries can be studied simply by analysing the heat produced in the reaction. According to WO 97/32208, WO 98/15813 and Ind. Eng. Chem. Res. 1996, 35, pp. 4801-4803, an entire material library is studied for its useful properties using a thermosensitive camera. The disadvantage of the method is essentially that the thermosensitive camera reflects via the heat liberated only the degree of activity of the catalysts. For a number of reactions this information is sufficient (total oxidations, complete hydrations etc.) (see, inter alia, Holzwarth, A., Schmidt, H. W., Maier, W. F., Angewandte Chemie, 1998, 110, 19, 2788-2791; Reetz, M. T., Becker, M. H., Holzwarth, A., Angewandte Chemie, 1998, 110, 19, 2792-2795), but in other reactions, especially what are termed partial oxidations of hydrocarbons, to evaluate catalytic properties of a building block of a material library information on activity alone is not sufficient, since the selectivity of the building block in such reaction types generally plays a greater role than the activity.

WO 97/32208 refers in general terms without a more detailed disclosure to the fact that the detector of the apparatus can further comprise Raman spectroscopy, FT-IR spectroscopy, NMR, mass spectroscopy, gas chromatography, liquid chromatography and enzymatic or biological additions, etc.

Mass spectrometry, owing to its high sensitivity, has long occupied a position in the field of organic and pharmaceutical combinatorial chemistry. Recent work by Weinberg et al. demonstrates the possibility of employing mass spectrometric methods for high-speed screening of heterogeneous catalyst libraries (P. Cong, R. D. Doolen, Q. Fan, D. M. Giaqunta, S. Guan, E. W. McFarland, D. M. Poojary, K. Self, H. W. Turner, W. H. Weinberg, Angew. Chem. 111 (1999) 507; U.S. Pat. No. 5,959,297, WO 98/15969 A2, W. H. Weinberg, E. W. McFarland, P. Gong, S. Guan, Symyx Technologies, 1998; R. F. Service, Science 280 (1998) 1690). Weinberg and collaborators detect the $CO_2$ formed and the starting gases by mass spectrometry in the oxidation of CO by $O_2$ or NO on metal alloys of Rh, Pd, Pt and Cu. For this purpose they use a capillary bundle for spatially separated starting material feed and product removal in the form of a quartz capillary which is coupled to a mass spectrometer. Taking into account the method of synthesizing ternary metal alloys via radiofrequency cathode atomization and the use of various mask systems (U.S. Pat. Nos. 5,985,356, 6,004,617, WO96/11878, P. G. Schultz, X. Xiang, I. Goldwasser, Symyx Technologies, 1996), it can be seen how the above-cited patent literature also describes that the actual structure is much more complicated than the very schematic description in the publications. For catalyst amounts of from 2 to 4 µg on a catalyst element of 1.5 mm in diameter, even at conversion rates of from 80 to 90% and high selectivities, as is the case in the oxidation of CO, only very small amounts of product are formed. Thus a complex modification of the mass spectrometer with a second quadrupole mask ("ion guide") and the construction of a vacuum chamber system for separate analysis, sample pretreatment and actual testing are required. Especially, handling samples from the outside is made much more difficult. In this example also differentiation can actually only be via catalyst activities, the oxidation of CO by $O_2$ or NO to form $CO_2$ as the sole possible reaction product provides no information on the selectivity differences in the individual library members. In more complex reactions having a plurality of possible products which are frequently formed at low yields with different or similar selectivities, this method fails owing to the too small amounts of product.

Overall, the method of Weinberg et al. requires high financial expenditure and much equipment. The conditions of the catalytic testing and catalyst production must be termed highly idealized and remote from industrially relevant conditions. The applicability and use of the results obtained on a laboratory scale is questionable. Overall, the method demonstrates, however, the applicability in principle of mass spectrometry in combinatorial solid-state research.

In addition to Symyx, Maier and collaborators also describe a system for the mass-spectrometric scanning of libraries of heterogeneous catalysts (M. Orschel, J. Klein, W. F. Maier, Angewandte Chemie, 1999, 111, 18, 2961). This very simple process for the spatially resolved determination of catalytic activities and selectivities using mass spectrometry results from coupling an automated synthesis machine to a commercial gas analyser. It is shown that using a suitable arrangement of feed and measuring capillaries different selectivities of heterogeneously catalysed reactions on a catalyst library open to the outside can be reliably and rapidly studied in a spatially resolved manner. Using as example the selective oxidation of propene with atmospheric oxygen at temperatures of from 250 to 450° C., the selective formations of acrolein, benzene and 1,5-hexadiene may be assigned to different catalyst materials. This arrangement is characterized by the use of relatively large amounts of catalyst (from 1 to 2 mg) in contrast to Symyx and by the fact that an open system is employed (operating under atmospheric pressure, generation of "microreactors" by attaching a capillary bundle of starting material feed and product removal). However, in this case also the overflow principle corresponds only remotely to actual reaction conditions resembling those in industry. If a large material library is scanned completely, the time factor due to the sequential measurement of each individual measuring building block is virtually unacceptable; in addition, the catalysts, owing to the integral heating of the overall library, are exposed to very different thermal conditions depending on whether they are tested at the beginning or at the end of a run. In comparison with parallel simultaneous recording of an entire library in IR thermography, mass-spectrometric sequential scanning must be classified as a very slow method. On p. 2965 at the end of this article there is also a reference to the possibility of combining mass spectrometry and IR thermography without any details being disclosed in this regard.

SUMMARY OF THE INVENTION

In view of the above-described information, the object underlying the present invention was to provide a process and an apparatus for determining useful properties of individual building blocks of a material library which do not have the disadvantages of the methods previously used in the analysis of such material libraries and, in addition, provide in a simple and rapid manner information on useful properties, preferably catalytic properties, in this case in particular activity and selectivity, of building blocks of a material library.

These and other objects are achieved by a process for determining useful properties of individual building blocks of a material library comprising a substrate having at least two individual building blocks in at least two sections which are separated from one another. According to an embodiment of the present invention, the process comprises (iii) simultaneous measurement of at least one first parameter at at least two, preferably all, sections with a first sensor, the first parameter giving an indication of a first property of the respective building blocks, and (iv) measurement of at least one further parameter with at least one further sensor, the further parameter giving an indication of a further property of the respective building blocks.

In a particularly preferred embodiment, the at least one further parameter is measured only for a selected group of sections, the choice of a section for measuring the second parameter depending on the respective result of the measurement of the first parameter.

The present invention further relates to a process which, in addition to the abovementioned steps, comprises the following further preceding step of (i) production of a material library comprising a substrate having at least two individual building blocks in at least two different substrate sections which are separated from one another. The process can further comprise the following further step (ii) before step (iii) and, if it is carried out, after step (i): (ii) introduction of at least one starting material into at least two substrate sections which are separated from one another of a material library for carrying out a chemical or physical or chemical and physical conversion of the starting material in the at least two substrate sections separated from one another, in each case in the presence of the corresponding building block, obtaining in each case an effluent stream containing at least one conversion product and/or starting material.

According to another embodiment of the present invention, an apparatus for carrying out the above processes comprises means for receiving at least two individual building blocks comprising a substrate having at least two different sections separated from one another, means for introducing at least one starting material, a first sensor for measuring a first parameter, and at least one further sensor for measuring at least one further parameter. The apparatus further comprises a data processing device which selects the sections for measuring the second parameter on the basis of the results of measurement of the first parameter according to predefinable criteria.

According to one aspect of the invention, the material library relates to catalysts. The first sensor in this aspect is preferably an infrared camera which records as first parameter the temperature development of at least two, preferably at least 30% of, further preferably at least 50% of, and in particular all, sections simultaneously, the respective temperature changes of these sections being a measure of the activity of the building blocks present in the sections. Preferably, only those sections are chosen for measuring the at least one further parameter in which the extent of the temperature change indicates a sufficient activity. The at least one further sensor is according to this aspect a spectroscopic sensor which, as a further parameter, provides data with respect to selectivity. Analytical methods of this type can be: GC, MS, GC/MS, Raman spectroscopy and other suitable methods. Preferably, the further sensor is a mass spectrometer, in particular a quadrupole mass spectrometer.

Preferably, the inventive process is carried out in such a manner that two parameters are determined, further preferably in a manner as described above, in particular using an infrared camera as first sensor and a mass spectrometer as second sensor.

Further features and advantages of the invention, as well as the structure and operation of various embodiments of the invention, are described in detail below with reference to the accompanying drawings.

BRIEF DESCRIPTION OF THE DRAWINGS

The present invention will now be described in detail with reference to the accompanying drawings, in which.

DETAILED DESCRIPTION OF THE PREFERRED EMBODIMENTS

Figure 1:
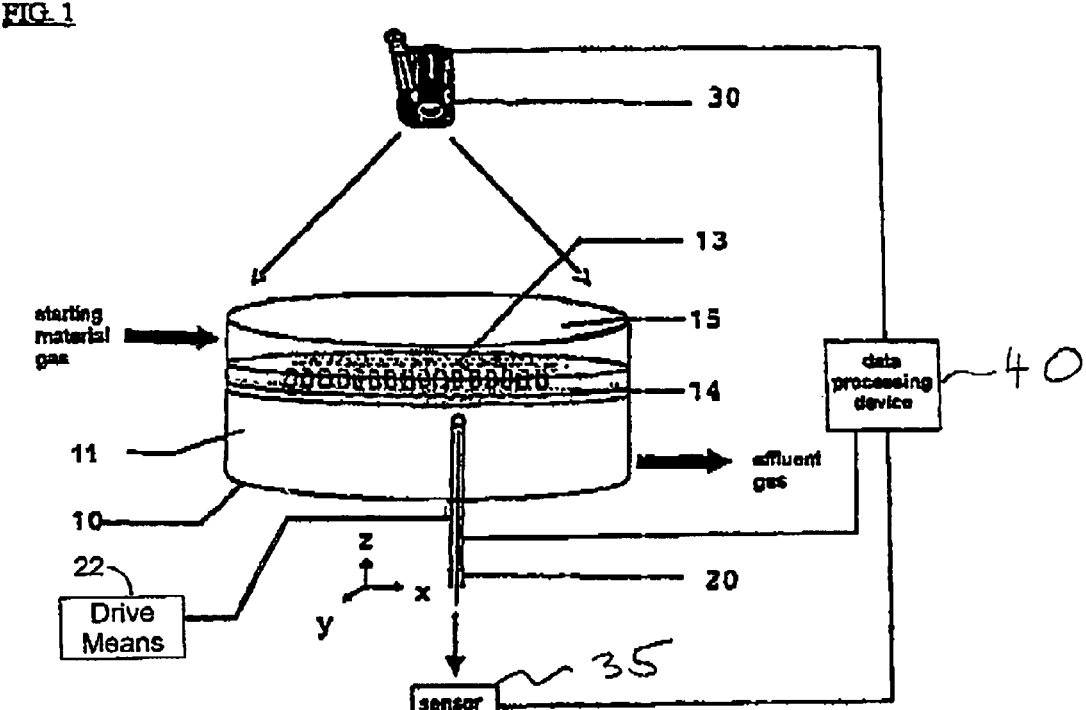
FIG. 1 shows a diagrammatic arrangement of a first exemplary embodiment of the inventive apparatus.

The present invention provides a process and an apparatus for determining useful properties of individual building blocks of a material library which do not have the disadvantages of the methods previously used in the analysis of such material libraries and, in addition, provide in a simple and rapid manner information on useful properties, preferably catalytic properties, in this case in particular activity and selectivity, of building blocks of a material library.

For purposes of the description, the following definitions are provided.

The term "material library" used in the context of the present invention describes here an arrangement of at least two, preferably up to 10, further preferably up to 100, in particular up to 1000 and further preferably up to 100,000, building blocks which are situated in at least two different substrate sections which are separated from one another.

The term "building block" describes a single defined unit which is situated in the respective substrate sections which are separated from one another and which single defined unit can consist of one or more components.

The term "substrate" comprises in principle all devices having a rigid or semirigid surface which can be either flat or have depressions or boreholes or channels. The substrate must be suitable for physically separating from one another the at least two individual building blocks in the at least two different sections which are separated from one another. The building blocks can be disposed in the substrate one-, two- or three-dimensionally, that is to say next to one another and one above the other in various planes.

Preferably the substrate comprises continuous channels in parallel and can have, inter alia, a wire grid or foamed ceramic.

Further preferably it is a tube-bundle reactor. The geometric disposition of the individual sections to one another can be chosen freely in this case. For example, the sections can be disposed in the manner of a row (quasi one-dimensionally), a chessboard pattern or honeycomb-like (quasi two-dimensionally). In the case of a substrate having parallel continuous channels, preferably a tube-bundle reactor having a multiplicity of tubes parallel to one another, the disposition becomes clear when considering a cross-sectional area perpendicular to the longitudinal axis of the tubes: a surface results in which the individual tubular cross sections reflect the different regions at a distance from one another. The sections or tubes can, for example for tubes having a circular cross section, also be present in a dense packing, so that different rows of sections are disposed offset from one another.

The term substrate describes a three-dimensional article which has a multiplicity (at least two) of "sections". Preferably, these sections are tubes, but they can also be individual sections physically separated from one another of a substrate which is flat or has depressions, for example in the form of a spotting plate. Preferably, the sections are constructed as channels. The channels thus connect two surface regions of the substrate and run through the substrate. Preferably, the channels are essentially, preferably completely, parallel to one another. The substrate in this case can be made up of one or more materials and can be solid or hollow. It can have any suitable geometric shape. Preferably it has two surfaces which are parallel to one another, in each of which there is an opening of the channels. The channels in this case preferably run perpendicularly to these surfaces. An example of a substrate of this type is a parallelepiped or cylinder in which the channels run between two parallel surfaces. However, a multiplicity of similar geometries is also conceivable.

The term "channel" describes a connection running through the substrate between two openings present on the body surface, which connection permits, for example, the passage of a fluid through the body. The channel can have any desired geometry in this case. It can have a cross-sectional area which is variable over the length of the channel or it can preferably have a constant channel cross-sectional area. The channel cross section can have, for example, an oval, round or polygonal periphery having straight or curved connections between the points of the polygon. Preference is given to a round or equilateral polygonal cross section. Preferably, all channels in the body have the same geometry (cross section and length) and run parallel to one another.

The term "tube bundle reactor" describes combined parallel dispositions of a multiplicity of channels in the form of tubes, with the tubes being able to have any desired cross section. The tubes are disposed in a fixed spatial relationship to one another, are preferably spatially separated from one another and are preferably enclosed by a housing or shell which includes all tubes. Through this, for example, a heating medium or cooling medium can be passed through the shell, so that all tubes are heated or cooled uniformly.

The term "block of a solid material" describes a substrate made of a solid material (which in turn can be made up of one or more starting materials) which has the channels, for example in the form of boreholes. The geometry of the channels (boreholes) can be selected freely, as described in general for the channels above. The channels (boreholes) need not be introduced by drilling, but can be left open, for example even during moulding of the solid body/block, for instance by extrusion of an organic and/or inorganic moulding composition (for example by an appropriate nozzle geometry during extrusion). In contrast to the tube bundle reactors or heat exchangers, the space in the body between the channels in the block is always filled by the solid material. Preferably, the block is made up of one or more metals.

The term "predetermined" means that, for example, a number of different or identical building blocks, for example catalysts or catalyst precursors, are introduced to, for example, a tube bundle reactor or heat exchanger in such a manner that the assignment of the respective building blocks, for example catalysts or catalyst precursors, to the individual tubes is recorded and can be retrieved later, for example when determining useful properties, for example activity, selectivity and/or long-term stability of the individual building blocks, for example catalysts, in order to enable clear assignment of defined measured values to defined building blocks. Preferably, the building blocks are prepared and distributed onto the different regions under computer control, the respective composition of a building block and the position of the section in the substrate, for example tube bundle reactor, into which the catalyst or catalyst precursor is introduced being stored in the computer and being able to be retrieved later. The term "predetermined" thus serves for differentiation from a chance or random distribution of the individual building blocks among the substrate sections.

Thus the present invention relates in particular to a process of the type in question here, which is characterized in that the substrate is a tube bundle reactor or heat exchanger and the regions are channels, preferably tubes, or the substrate is a block of a solid material which has regions, preferably channels.

In addition, the at least two individual building blocks have preferably useful properties and further preferably are heterogeneous catalysts and/or their precursors, further preferably inorganic heterogeneous catalysts and/or their precursors and in particular solid catalysts or supported catalysts and/or their precursors. They are present here preferably in each case as catalyst bed, tube-wall coating or auxiliary coating. In the context of the present processes the individual building blocks can be identical or different from one another. If they are different from one another, the selected reaction conditions during the reaction can be identical or different; if the building blocks are identical, preferably the reaction conditions are different in the individual regions.

The process according to preferred embodiments of the present invention relates to the following steps.

Step (i)

The material libraries and/or the individual building blocks present therein may be prepared, as described in general terms below, with reference being made with respect to further details to WO 99/19724, WO 96/11878 and WO 99/41005. In detail, the following methods may be mentioned:

Processes for applying thin films, for example electron beam vaporization, sputtering, thermal vaporization, plasma vaporization, molecular beam epitaxy, precipitation from the gaseous phase, precipitation by a modulatable laser; co-precipitation and impregnation; impregnation of suitable support materials which, for example porous silicon dioxide or aluminium oxide, as previously are each introduced into the substrate sections. The active component(s) can be applied by introducing solutions, suspensions or pastes, each of which comprise the active component(s) or one or more suitable compounds thereof. With respect to the supports which can be used, there are no restrictions, reference here in particular being made to porous and monolithic supports.

In addition, it is also possible to prepare material libraries which comprise homogeneous building blocks, for example homogeneous catalysts. For this purpose, for example, organometallic or inorganometallic compounds and/or any desired complex molecules, for example enzymes, are used, employing a suitable device, for example a suitable pipette having a plurality of channels in order to introduce the building blocks into the appropriate sections separated from one another.

In particular, the material libraries studied according to the invention may be prepared by the following procedures which are described by way of example with reference to the inorganic heterogeneous catalysts and/or their precursors also preferably used in the context of the present invention. Reference is made to WO 99/41005 with respect to further details of the procedures (a) to (f) described below.

Procedure (a) comprises the following steps:

a1) Production of solutions, emulsions and/or dispersions of elements and/or element compounds of the elements present in the catalyst and/or catalyst precursor, and if appropriate of dispersions of inorganic support materials, a2) if appropriate introduction of adhesion promoters, binders, viscosity regulators, pH-regulating agents and/or solid inorganic supports into the solutions, emulsions and/or dispersions, a3) simultaneous or sequential coating of the substrate channels with the solutions, emulsions and/or dispersions, a predetermined amount of the solutions, emulsions and/or dispersions being introduced into each channel in order to obtain a predetermined composition, and a4) if appropriate heating the coated body, in the presence or absence of inert gases or reactive gases, to a temperature in the range from 20 to 1500° C. for drying and if appropriate sintering or calcining the catalysts and/or catalyst precursors.

Procedure (b) comprises the following steps:

b1) Production of solutions, emulsions and/or dispersions of elements and/or element compounds of the elements present in the catalyst and/or catalyst precursor, and if appropriate of dispersions of inorganic support materials, b2) if appropriate introduction of adhesion promoters, binders, viscosity regulators, pH-regulating agents and/or solid inorganic supports into the solutions, emulsions and/or dispersions, b3) simultaneous or sequential coating of the catalyst supports present in the substrate channels with the solutions, emulsions and/or dispersions, a predetermined amount of the solutions, emulsions and/or dispersions being introduced into each channel in order to obtain a predetermined composition on the catalyst supports, and b4) if appropriate heating the substrate together with the coated catalyst supports in the channels, in the presence or absence of inert gases or reactive gases, to a temperature in the range from 20 to 1500° C. for drying and if appropriate sintering or calcining the catalysts and/or the catalyst precursors.

Procedure (c) comprises the following steps:

c1) Production of solutions, emulsions and/or dispersions of elements and/or element compounds of the chemical elements present in the catalyst and/or catalyst precursor, and if appropriate of dispersions of inorganic support materials, c2) mixing predetermined amounts of the solutions, emulsions and/or dispersions and if appropriate precipitation aids in one or more reaction vessels operated in parallel, c3) if appropriate introduction of adhesion promoters, binders, viscosity regulators, pH-regulating agents and/or solid inorganic supports into the resultant mixture(s), c4) coating one or more predetermined channels of the substrate with the mixture or a plurality of mixtures, c5) repeating steps c2) to c4) for other substrate channels until the channels are coated with the respectively predetermined catalyst compositions and/or catalyst precursor compositions, c6) if appropriate heating the coated substrate, in the presence or absence of inert gases or reactive gases, to a temperature in the range from 20 to 1500° C. for drying and if appropriate sintering or calcining the catalysts and/or catalyst precursors.

Preferably, the procedure comprises the following steps:

c1) Production of solutions of element compounds of the chemical elements present in the catalyst except for oxygen, and if appropriate of dispersions of inorganic support materials c2) mixing predetermined amounts of the solutions or dispersions and if appropriate precipitation aids in one or more reaction vessels operated in parallel with precipitation of the chemical elements present in the catalyst, c3) if appropriate introduction of adhesion promoters, binders, viscosity regulators, pH-regulating agents and/or solid inorganic supports into the resultant suspension, c4) coating one or more predetermined tubes of the tube bundle reactor or heat exchanger with the suspension, c5) repeating steps c2) to c4) for different tubes of the tube bundle reactor or heat exchanger until the tubes are coated with the respectively predetermined catalyst compositions, c6) heating the coated tube bundle reactor or heat exchanger, in the presence or absence of inert gases or reactive gases, to a temperature in the range from 20 to 1500° C. for drying and if appropriate sintering or calcining the catalysts.

Procedure (d) comprises the following steps:

d1) Production of solutions, emulsions and/or dispersions of elements and/or element compounds of the chemical elements present in the catalyst and/or catalyst precursor, and if appropriate of dispersions of inorganic support materials, d2) mixing predetermined amounts of the solutions, emulsions and/or dispersions and if appropriate precipitation aids in one or more reaction vessels operated in parallel, d3) if appropriate introduction of adhesion promoters, binders, viscosity regulators, pH-regulating agents and/or solid inorganic supports into the resultant mixture(s), d4) coating catalyst supports present in one or more predetermined substrate channels with the mixture or one or more of the mixtures, d5) repeating steps d2) to d4) for other (that is to say generally not yet coated) catalyst supports in the substrate channels until the (preferably all) catalyst supports present in the substrate channels are coated with the respectively predetermined (generally differing from one another) catalyst compositions and/or catalyst precursor compositions, d6) if appropriate heating the substrate, together with the coated catalyst supports in the channels, in the presence or absence of inert gases or reactive gases, to a temperature in the range from 20 to 1500° C. for drying and if appropriate sintering or calcining the catalysts and/or catalyst precursors.

In this case the adhesion strength of the channels (for example of the inner surface of the tubes) of the substrate or of the catalyst supports can be increased before the coating by chemical, physical or mechanical pretreatment of the inner walls of the channels (for example inner tubes) or of the catalyst supports or by applying an adhesion layer. This relates in particular to the procedures (a) and (c), and (b) and (d), respectively.

Procedure (e) comprises the following steps:

e1) Production of different heterogeneous catalysts and/or their precursors in the form of solid catalysts having a predetermined composition, e2) charging in each case one or more predetermined substrate channels which are secured against the heterogeneous catalysts falling out with in each case one or more of the heterogeneous catalysts and/or their precursors having a predetermined composition, e3) if appropriate heating the body together with the heterogeneous catalysts and/or their precursors in the channels, in the presence or absence of inert gases or reactive gases, to a temperature in the range from 20 to 1500° C. for drying and if appropriate sintering or calcining the catalysts and/or catalyst precursors.

Procedure (f) comprises the following steps:

f1) coating and if appropriate heating predetermined catalyst supports for producing predetermined supported catalysts in the manner defined above in process b) or d) outside the body, f2) introducing the supported catalysts into predetermined substrate channels, f3) if appropriate heating the charged substrate, in the presence or absence of inert gases or reactive gases, to a temperature in the range from 20 to 1500° C. for drying and if appropriate sintering or calcining the catalysts.

Preferably, here, the external shape of the supported catalysts corresponds to the shape of the channel interior in the body, at least substantially, preferably approximately or completely.

The procedures outlined above are suitable for preparing a multiplicity of catalyst systems, as described, for example, in G. Ertl, H. Knözinger, J. Weitkamp, Editors "Handbook of Heterogeneous Catalysis", Wiley—VCH, Weinheim, 1997.

With respect to further details regarding the production of a material library according to (i) of the inventive process, reference is made to the section "Production of the inorganic heterogeneous catalyst arrays" of WO 99/41005. In this section, the production of a material library (there termed "array") is described in detail with reference to producing a material library of inorganic heterogeneous catalysts. The content of this section of WO 99/41005 is, moreover, incorporated in its entirety in the context of the present invention by reference. Obviously, the concept described there may also be applied to other building blocks, for example homogeneous catalyst systems, in particular organometallic systems, organic substances, for example pharmacological active compounds, polymers, composite materials, in particular those made of polymers and inorganic materials. In principle, the inventive process is applicable to all areas of the technique in which formulations, that is to say compositions having more than one constituent, are produced and are studied for their useful properties. Fields of application outside material research are, for example, drug formulations, formulations of foods and food supplements, feeds and cosmetics.

Accordingly, the present invention is not restricted to determining the useful properties of certain catalyst materials and catalyst compositions. The production of the abovementioned mixtures can be carried out here in parallel or sequentially and is generally carried out in automated form, for example using an automated pipetting system or pipetting robot, by inkjet processes, as described, for example, in U.S. Pat. No. 5,449,754, and automated sputtering or electrolysis processes.

In addition to the procedures (a) to (f) described above, obviously, it is also possible to prepare different heterogeneous catalysts in the form of solid catalysts or supported catalysts by known processes, for example combinatorial processes, having a predetermined composition and charging in each case one or more predetermined sections, preferably tubes of a tube bundle reactor or heat exchanger or tubes or auxiliary supports introduced into these, with each of these prefabricated heterogeneous catalysts.

Step (ii)

The chemical or physical, or chemical and physical, conversion of the starting material in the at least two substrate sections which are separated from one another, with an effluent stream comprising at least one conversion product being obtained, according to step (ii) can be carried out as follows.

Firstly, if necessary, the catalyst can be activated in the substrate. This can be carried out by thermal treatment under inert gases or reactive gases or other physical and/or chemical treatments.

The substrate is then brought to a desired reaction temperature and then a fluid starting material, which can be a single compound or a mixture of two or more compounds, is passed through or along one, a plurality of, or all the sections, preferably channels, of the substrate.

The fluid starting material consisting of one or more reactants is generally in the liquid state, or preferably in the gaseous state. Preferably, oxidation catalysts, for example, are tested by parallel or sequential impingement of individual, a plurality of, or all sections, preferably tubes of a coated tube bundle reactor, with a gas mixture comprising one or more saturated, unsaturated or polyunsaturated organic starting materials. Those which may be mentioned in this case are, for example, hydrocarbons, alcohols, aldehydes etc., and oxygen-containing gases, for example air, $O_2$, $N_2O$, $NO$, $NO_2$, $O_3$ and/or, for example, hydrogen. Furthermore, an inert gas, for example nitrogen or a noble gas, may also be present. The reactions are generally carried out at temperatures of from 20 to 1200° C., preferably from 50 to 800° C., and in particular from 80 to 600° C., the parallel or sequential separate removal of the respective gas streams from individual, a plurality of, or all sections being ensured by means of a suitable device.

The resultant effluent stream comprising at least one reaction product is then collected either from individual substrate sections or a plurality of substrate sections and preferably analysed separately, sequentially or preferably in parallel, if analysis of the effluent stream after the inventive processes is required for the respective section.

A plurality of reactions, in each case interrupted by a purge step with a purge gas, can be carried out sequentially at the same or different temperatures and analysed. Obviously, identical reactions at different temperatures are also possible.

Preferably at the start of the process, the collected effluent stream of the entire library is analysed in order to establish whether a reaction has taken place at all. In this manner, groups of building blocks may be analysed very rapidly as to whether they have any useful properties, for example catalytic properties, at all. Obviously, after carrying out this "coarse screening", individual groups of building blocks may in turn be analysed together in order to establish in turn which group of building blocks, if there are a plurality of such groups of building blocks present in the material library, have catalytic properties.

The invention permits the automated preparation and catalytic testing for the purpose of mass screening of, for example, heterogeneous catalysts for chemical reactions, in particular for reactions in the gas phase, very particularly for partial oxidations of hydrocarbons in the gas phase with molecular oxygen (gas-phase oxidations).

Reactions and conversions suitable for study are described in G. Ertl, H. Knözinger, J. Weitkamp, Editor, "Handbook of Heterogeneous Catalysis", Wiley—VCH, Weinheim, 1997. Examples of suitable reactions are principally listed in this reference in volumes 4 and 5 under numbers 1, 2, 3 and 4.

Examples of suitable reactions are the decomposition of nitrogen oxides, the synthesis of ammonia, the oxidation of ammonia, oxidation of hydrogen sulphide to sulphur, oxidation of sulphur dioxide, direct synthesis of methylchlorosilanes, oil refining, oxidative coupling of methane, methanol synthesis, hydrogenation of carbon monoxide and carbon dioxide, conversion of methanol to hydrocarbons, catalytic reforming, catalytic cracking and hydrocracking, coal gasification and liquefaction, fuel cells, heterogeneous photocatalysis, synthesis of ethers, in particular MTBE and TAME, isomerizations, alkylations, aromatizations, dehydrogenations, hydrogenations, hydroformylations, selective or partial oxidations, aminations, halogenations, nucleophilic aromatic substitutions, addition and elimination reactions, dimerizations, oligomerizations and metathesis, polymerizations, enantioselective catalysis and biocatalytic reactions and for material testing, and, in this case, in particular for determining interactions between two or more components on surfaces or substrates, in particular in the case of composite materials.

The effluent streams of the respectively selected sections comprising at least one reaction product and/or the starting material which is preferably obtained separately from the individual sections are preferably removed via a device which is connected gas-tightly to the respective sections. In particular those which may be mentioned are sample removal using suitable flow guidance, for example valve circuits and mobile capillary systems (sniffing apparatus). In this manner the individual effluent streams of the individual, plurality of, or all sections can be removed separately and then analysed separately via a valve circuit.

The, for example, computer-controlled mechanically movable "sniffing apparatus" comprises a sniffing line or sniffing capillary for the effluent stream to be taken off which is positioned essentially automatically on, in/or above the exit of the respective section and then takes off the effluent stream. Details with respect to the arrangement of such a "sniffing apparatus" may also be taken from WO 99/41005 which has been cited repeatedly above.

Step (iii)

The measurement of the first parameter under step (iii) may be carried out at all sections.

In principle, there is freedom of choice of the measurement method, but it should be in this case a relatively rapid and simple measurement method, since in some preferred embodiments a great number of sections must be analysed. The purpose of this first measurement is preselection of those sections which are to be analysed under step (iv).

The preferred measurement method which may be mentioned is infrared thermography which may be accomplished simply using an infrared camera. In this case the temperature development of the individual sections may be taken from the infrared image recorded, preferably using digital image processing. In the event of a small number of sections, if appropriate, a temperature sensor may be assigned to each individual section, for example a pyrometric element or a thermocouple. The results of temperature measurement for the individual sections can all be passed to a data processing system, which preferably controls the inventive process.

In order to eliminate substantially interfering environmental effects, the substrate together with the sections to be tested should preferably be situated in a thermally insulated housing having a controlled atmosphere. If an infrared camera is used, this should preferably be situated outside the housing, observation of the substrate being enabled by infrared-transparent windows, in particular made of sapphire, zinc sulphide, barium difluoride, sodium chloride etc. On the basis of the results of measurement of the first parameter, using a data processing system or a computer, those sections are selected from which the second parameter is to be measured. In this case various selection criteria are conceivable. Firstly, those sections can be selected for which the first parameter is "better" than a predetermined limit value, or secondly the "best" x% of all sections on a substrate can alternatively be selected for measuring the second parameter. The said minimum requirements or the number of sections to be selected depends firstly on the respective quality requirements of the materials to be tested and secondly on the time which is available for testing a substrate.

If there is a predetermined limit value with respect to the minimum requirement of the first measured value, this need not be constant for all sections of a substrate, but it can, for example, be predetermined as a function of other properties of the respective building components for the individual sections.

Step (iv)

The measurement of the at least one further parameter is preferably carried out on the effluent stream of the selected sections. In principle the further sensor (See FIGS. 1 and 2, reference nos. 35, 135) is not subject to any restrictions provided that it is suitable for measuring a further parameter which gives indications of a further property of the building block under test.

Preferably, the further sensor is based on a spectroscopic method which is selected from the group comprising mass spectrometry, gas chromatography, a combination of these two techniques, Raman spectroscopy and Fourier transformation (FT-IR) spectroscopy.

On the basis of these preferred methods, more precise information on the effluent stream of the respective sections or building blocks may be obtained. Using these spectroscopic methods, the concentration of a desired product, or the concentration of parallel products and the residual concentration of the starting materials can be determined, from which, for example, for catalytic building blocks, information on selectivity may be derived.

For mass spectroscopy, preferably a quadrupole mass spectrometer is used, although TOF mass spectrometers (real-time spectrometers) are conceivable. The effluent stream of the sections under test is fed to the mass spectrometer, or other sensors, preferably via a pipe system, with this being, in particular, a sniffing capillary 20, which is positioned in the effluent stream of the respective sections using an XYZ robotic system 22.

For optical systems such as Raman spectrometers and FT-IR spectrometers, it is conceivable that light is directed onto each of the sections under test and is received from each of the sections under test using scanning mirrors.

Figure 2:
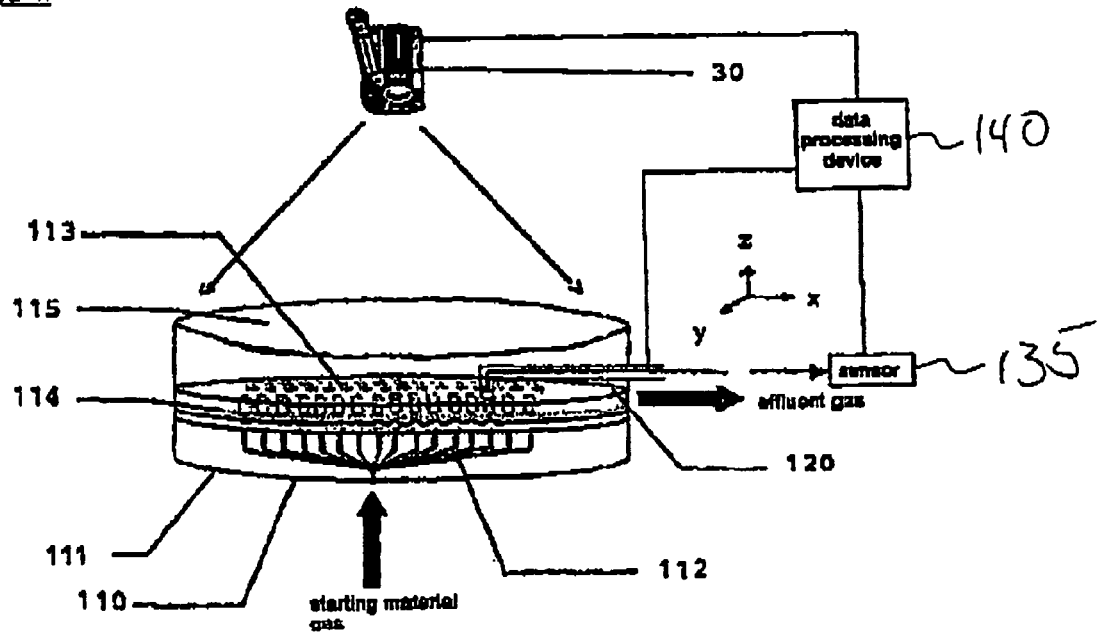
FIG. 2 shows a diagrammatic view of a second exemplary embodiment of the inventive apparatus.

According to another embodiment of the present invention, an apparatus is provided as shown in FIGS. 1 and 2. The inventive apparatuses 10; 110 each have a housing 11; 111, which is provided with at least one heater (not shown) in order to control the temperature in the housing.

The cylindrical housing 11; 111 has a planar support which is constructed as a wire grid or foamed ceramic 14; 114 and in which parallel cylindrical sections 13; 113 are arranged for receiving the building blocks. In the embodiment shown in FIG. 1, the starting material gas is introduced above the support into the entire space above the sections 13 and can flow downwards through the sections, the exhaust gas leaving the housing at an outlet (which is not shown). In contrast thereto, in the case of the apparatus 110 shown in FIG. 2, the starting material gas is passed specifically by means of a pipe system 112 below the respective cylindrical sections 113. The gas then flows through the cylindrical sections, and if appropriate the planar support 114, the reaction products or the remaining starting material leaving the upper housing part as exhaust gas through an outlet (which is not shown).

The exemplary embodiments shown have as the first sensor an infrared camera which is positioned so that it can determine simultaneously the temperature of all cylindrical sections. For this purpose the temperature values in the temperature distribution recorded as an image are each assigned to the sections whose position corresponds to an image region.

The assignment can be made according to varying criteria. Firstly, the temperature of each section can be retrieved by determining the temperature in each image region which corresponds to a section position. Secondly, the temperature distribution observed in the image can also be used as a starting point, with the associated sections only being determined for temperature values of "interest", for example extreme values or values within or below or above one or two threshold values. The second procedure is recommended, in particular, for systems having a large number of sections in which only "particularly promising" sections are to be studied further.

The infrared camera 30 is preferably positioned outside the housing in order to protect it from the starting materials and products in the housing. Observation of the substrate even from outside the housing is possible via an infrared-transparent window 15, for example a sapphire disc. Other suitable materials for the disc are calcium fluoride, barium fluoride, zinc sulphide etc. As a second sensor, a mass spectrometer (35; 135) is provided, to which the effluent stream from selected sections is fed via a capillary 20; 120.

The upper layer of the substrate 14; 114 preferably consists of a material whose emissivity properties ideally approach those of a black-body radiator, with particular preference being given to natural slate. In this manner, interference in the temperature measurement by the substrate is substantially eliminated.

The capillary for this purpose is positioned via an XY robot or an XYZ robot (not shown) with its intake orifice in each case in the effluent stream of a selected section.

The robot is controlled via the data processing system (40, 140), which selects the sections for the second measurement on the basis of the measured results of the first measurement.

The above-described combination of an integral analytical method which may be employed with relatively low expenditure to a multiplicity of samples or sections with a more precise or more complex analytical method which, however, is only carried out for selected sections, allows, for example, in the development of catalysts, the activity and selectivity of materials having promising activity to be determined very rapidly and effectively.

Finally, reference may also be made to the fact that what is termed the "sniffing capillary" would also be usable as a sample inlet system for other analytical techniques, for example chromatographic methods.

Other expedient analytical combinations are IR thermography/GC-MS, IR thermography/Raman spectroscopy, IR thermography/dispersive FT-IR spectroscopy, colour detection using chemical indicator/MS, colour detection using chemical indicator/GC-MS, colour detection using chemical indicator/dispersive FT-IR spectroscopy and others.

As a further preferred alternative embodiment of the above-described embodiments, an integrated apparatus comprising a heatable substrate and carriers is disclosed.

According to the invention the apparatus is characterized in that the substrate comprises a block made of electrically conducting material exhibiting sections having the form of channels, said block being heatable by the principle of a resistance heating, whereas the substrate is characterized in that each channel comprises a carrier.

In principle, an electrically conducting, preferably metallic material being heatable via a resistance heating comprising preferably channels in numbers, shape and orientation, as respectively described above, serves as a substrate. Further materials that may be used instead of metals as the substrate are, e.g., alloys, particularly metal alloys, graphite and ceramics.

On a preferably round metal disk, which has holes, e.g., in the form of a narrow screen, an array of channels is generated. Then, a ceramic carrier may be directly synthesized into these channels.

According to the invention the substrate is characterized in that the carrier is synthesized into the channels.

By way of particularly the "in situ synthesis" of the ceramic carrier into the channels, each channel may individually be provided with catalytic active components. Each individual channel penetrates the disk and exhibits a certain cross section. With regard to the plurality of possible shapes of the cross section of the channel, reference is made to the above description thereof.

The carrier may preferably be a porous ceramic material, such as $SiO_2$, $Al_2O_3$, $ZrO_2$, $TiO_2$, ceolites, mixtures thereof, oxides, carbides, foam ceramics, which are filled into the channels by means of "in situ synthesis", such that these channels are preferably completely filled. Due to the pore size distribution in the range of large meso pores or macro pores, this filling of the channel allows for preferably gas mixtures of starting materials to flow through these channels. The pore size lies preferably at values of larger than 20 nm, preferably within the micrometer to millimeter range.

Furthermore the substrate according to the invention is characterized in that the carrier and/or the channel comprises at least one building block.

By means of conventional coating methods, such as dip-coating, spraying processes, sequential impregnation of the channels, integral (simultaneous) coating of all channels, sol-gel-processes, colloidal solutions, etc., the individual channels may be provided with building blocks (active components), which are preferably different from each other. This provision is preferably carried out automatically, e.g. by way of a robotic.

The construction of this substrate having dimensions, which are preferably adapted to the apparatus according to the invention, renders it possible to integrate the substrate into the apparatus according to the invention without any problems via an easy modification of the reactor.

This concept allows for a fast modular change of individual substrates (material libraries). This results in a more effective testing and analysis of individual building blocks with regard to preferably catalytic properties.

The substrates may exhibit a statistical coating of preferably different building blocks or concentration lines of preferably four materials, which are preferably a coating having a concentration gradient. Other coating variants are also possible, e.g. by forming sections of different materials having a shape which is different from lines or rows, e.g. a polygonal form. All coatings are provided automatically, e.g. with a robotics system.

In a preferred process for generating a material library comprising multiple components having a large diversity, the substrate together with the channels and carriers is immersed in e.g. a solution of an active component and subsequently again pulled out. By increasing the velocity during such a "dip coating process", the coating of a first component having a concentration gradient is possible. Subsequently, the substrate is dried and rotated by 90°. The same procedure is repeated when coating the preferably three more components. Subsequently, the substrate is treated at elevated temperature, i.e. between 100 and 1000° C. for a longer period of time, such that on the individual sections of the substrate new compounds are formed. In this manner, it is possible to form a new compound in each individual channel, which may be tested with regard to preferably useful properties.

As an alternative to the "dip coating", spray processes may be used, wherein one or more nozzles provide individual sections of the substrates with solutions of active components in variable velocity.

By providing voltage on contacts, which are preferably provided outside of the substrate, the preferably disk-like substrate exhibiting a number of carriers may, dependant on the height of the provided voltage, be brought to a freely chosen temperature, which lies under the melting point of the respective material of the substrate in a very homogenous manner. Each individual channel of the substrate provides for a practically punctual heat transfer on e.g. carrier and building block by an electrically conducting enclosure.

The preferably disk-like substrate preferably exhibits a thickness in the range of 1 mm to 30 cm, particularly preferred in the range of 5 to 50 mm. The disk-like substrate exhibits a diameter preferably in the range of 1 cm to 100 cm, particularly preferred 5 cm to 50 cm.

The diameter of the channels lies preferably in the range of 1 µm to 10 cm, particularly preferred in the range of 1 to 10 mm.

Depending on the diameter of the substrate and the channels, the substrate may exhibit 1 to 100,000, preferably 100 to 2000 and particularly preferred 500 to 1000 channels.

While the invention has been described in detail and with reference to specific embodiments thereof, it will be apparent to one skilled in the art that various changes and modifications can be made therein without departing from the scope of the invention. Thus, the breadth and scope of the present invention should not be limited by any of the above-described exemplary embodiments.

What is claimed is:

1. A process for determining catalytic properties of individual building blocks of a material library disposed on a substrate provided in a housing, the process comprising:
   introducing a starting material to the building blocks to carry out a chemical or physical or chemical and physical conversion of the starting material and obtain for each building block an effluent stream containing a conversion product and/or the starting material;
   simultaneously measuring, with a first sensor, a temperature or temperature change of each building block;
   determining, automatically by a data processing system, which of the building blocks to include in a subset of the building blocks by comparing the temperature or temperature change with a predetermined limit value, the subset including fewer than all of the building blocks measured with the first sensor; and
   measuring, with a second sensor, a further parameter which is indicative of the selectivity of each of the building blocks in only the subset, wherein the selectivity is measured in the respective effluent streams by determining a concentration of the desired product, or a concentration of the parallel products and a residual concentration of the starting materials;
   wherein the first sensor and the second sensor are configured so as to be capable of conducting measurements with respect to the building blocks when the building blocks are supported on the substrate in the housing.

2. A process according to claim 1, further comprising, before the simultaneous measuring step, a step of producing the material library.

3. A process according to claim 1, wherein a portion of each effluent stream from each building block of the subset is passed to the second sensor via a sniffing capillary positioned in the effluent stream by means of a suitable drive means.

4. A process according to claim 3, wherein the drive means is controlled automatically by the data processing system.

5. A process according to claim 1, wherein the first sensor is an infrared thermography camera, and the temperature or temperature change of each building block is measured thermographically by the camera.

6. A process according to claim 5, wherein, in the simultaneously measuring step, the camera measures the temperatures of the building blocks simultaneously.

7. A process according to claim 1, wherein:
   the second sensor senses by a method selected from the group consisting of mass spectrometry, gas chromatography, gas chromatography/mass spectroscopy, Raman spectroscopy, and FT-IR spectroscopy; and measuring with the second sensor comprises passing a portion of an effluent stream of each building block of the subset to the second sensor for analysis by the second sensor.

8. A process according to claim 1, wherein the substrate comprises a tube bundle reactor or heat exchanger and has channels in which the building blocks are located.

9. A process according to claim 1, wherein the substrate comprises a block of a solid material which has channels.

10. A process according to claim 1, wherein the building blocks are heterogeneous catalysts and/or their precursors.

11. A process according to claim 10, wherein the building blocks are inorganic heterogeneous catalysts and/or their precursors.

12. A process according to claim 1, wherein the building blocks are solid catalysts or supported catalysts and/or their precursors.

13. A process according to claim 12, wherein each building block is present as a catalyst bed, tube-wall coating or auxiliary support coating.

14. A process according to claim 1, wherein the temperature or temperature change is indicative of the activity of the respective building blocks such that the step of determining which building blocks to include in the subset includes determining which of the building blocks has catalytic activity above a predetermined threshold.

15. A process according to claim 1, further comprising, before the simultaneous measuring step, a step of introducing to the building block a starting material that can undergo any of the following:
decomposition of nitrogen oxides, synthesis of ammonia, oxidation of ammonia, oxidation of hydrogen sulphide to sulphur, oxidation of sulphur dioxide, direct synthesis of methylchlorosilanes, oil refining, oxidative coupling of methane, methanol synthesis, hydrogenation of carbon monoxide and carbon dioxide, conversion of methanol to hydrocarbons, catalytic reforming, catalytic cracking and hydrocracking, coal gasification and liquefaction, heterogeneous photocatalysis, synthesis of ethers, isomerizations, alkylations, aromatizations, dehydrogenations, hydrogenations, hydroformylations, selective or partial oxidations, aminations, halogenations, nucleophilic aromatic substitutions, addition and elimination reactions, dimerizations, oligomerizations and metathesis polymerizations, enantioselective catalysis and biocatalytic reactions.

16. An apparatus comprising:
a substrate provided in a housing, the substrate being configured to support building blocks and receive a starting material dispensed to the building blocks;
a first sensor for measuring a temperature or a temperature change of the building blocks;
a second sensor for measuring a second parameter which is indicative of the selectivity of only a subset of the building blocks, the subset including fewer than all of the building blocks;
a data processing device that selects the building blocks to be included in the subset by comparing the first parameter with a predetermined limit value; and
a sniffing capillary;
wherein:
the first sensor and the second sensor are provided so as to be capable of conducting measurements with respect to the building blocks when the building blocks are supported on the substrate in the housing; and
the sniffing capillary is controlled automatically by the data processing device to position the sniffing capillary to receive an effluent stream from each building block of the subset, the sniffing capillary being configured to conduct the effluent streams to the second sensor.

17. An apparatus according to claim 16, wherein the first sensor is an infrared camera.

18. An apparatus according to claim 16, wherein the second sensor senses by a method selected from the group consisting of mass spectrometry, gas chromatography, gas chromatography/mass spectroscopy, Raman spectroscopy, and FT-IR spectroscopy.

19. An apparatus according to claim 18, wherein the second sensor is a quadrupole mass spectrometer.

20. An apparatus according to claim 16, wherein the substrate comprises a planar arrangement having a wire grid or foamed ceramic.

21. An apparatus according to claim 16, further comprising means for heating and/or cooling the housing.

22. An apparatus according to claim 16, wherein the housing has an IR-transparent window, and the first sensor comprises an infrared camera disposed outside the housing in front of the IR-transparent window.

23. An apparatus according to claim 16, wherein the substrate comprises a block made of electrically conductive material with channels, the block being heatable by resistance heating.

24. An apparatus according to claim 23, wherein each channel comprises a carrier.

25. An apparatus as defined in claim 24, wherein the carriers are synthesized into the channels.

26. An apparatus according to claim 24, wherein each carrier and/or channel supports a building block.

* * * * *